US008365758B2

(12) United States Patent
Maiocco (10) Patent No.: US 8,365,758 B2
(45) Date of Patent: Feb. 5, 2013

(54) BEVERAGE BARREL BLADDER SYSTEM AND APPARATUS

(75) Inventor: Mark A. Maiocco, Selah, WA (US)

(73) Assignee: Angels' Share Innovations, LLC., Yakima, WA (US)

( * ) Notice: Subject to any disclaimer, the term of this patent is extended or adjusted under 35 U.S.C. 154(b) by 434 days.

(21) Appl. No.: 12/589,927

(22) Filed: Oct. 30, 2009

(65) Prior Publication Data

US 2011/0101010 A1  May 5, 2011

(51) Int. Cl.
*B67D 7/72* (2006.01)
(52) U.S. Cl. ........ 137/209; 137/212; 137/213; 137/214; 137/429; 92/91; 92/92
(58) Field of Classification Search ............... 137/87.02, 137/87.05, 102, 206, 209, 212, 213, 214, 137/392, 429, 430; 426/132, 15, 592, 477; 92/91, 92
See application file for complete search history.

(56) References Cited

U.S. PATENT DOCUMENTS

| 262,773 | A | | 8/1882 | Hohl | 222/130 |
|---|---|---|---|---|---|
| 447,974 | A | | 3/1891 | Rheinstrom | 215/269 |
| 534,541 | A | * | 2/1895 | Wright | 222/386.5 |
| 713,708 | A | | 11/1902 | Spire | 215/269 |
| 3,083,098 | A | * | 3/1963 | Sullivan | 426/422 |
| 3,343,701 | A | | 9/1967 | Mahoney | 215/231 |
| 3,744,680 | A | * | 7/1973 | Salmonson | 222/399 |
| 4,211,115 | A | * | 7/1980 | Engebreth | 73/863.86 |
| 4,456,038 | A | * | 6/1984 | Gwaltney et al. | 141/95 |
| 4,763,803 | A | | 8/1988 | Schneider | 215/260 |
| 4,911,314 | A | | 3/1990 | Schneider | 215/228 |
| 5,458,165 | A | | 10/1995 | Leibmann, Jr. | 141/64 |
| 5,709,558 | A | * | 1/1998 | Dreyer et al. | 439/95 |
| 5,947,326 | A | * | 9/1999 | O'Hern et al. | 220/802 |
| 5,976,583 | A | * | 11/1999 | Mastrocola | 426/7 |
| 6,183,982 | B1 | | 2/2001 | Natasia | 435/41 |
| 6,312,588 | B1 | * | 11/2001 | Conrad et al. | 210/85 |
| 6,478,178 | B2 | | 11/2002 | Montgomery | 220/203.13 |
| 6,910,498 | B2 | * | 6/2005 | Cazden | 137/392 |
| 7,051,901 | B2 | * | 5/2006 | Hickert | 222/1 |
| 7,204,930 | B2 | * | 4/2007 | Nightingale | 210/741 |
| 7,878,214 | B1 | * | 2/2011 | Jansen et al. | 137/12 |
| 2004/0010263 | A1 | | 1/2004 | Boucher et al. | 606/99 |
| 2006/0032548 | A1 | * | 2/2006 | Cupples et al. | 141/95 |
| 2007/0209706 | A1 | * | 9/2007 | Wu | 137/209 |
| 2009/0139584 | A1 | * | 6/2009 | Schmitz et al. | 137/392 |

* cited by examiner

FOREIGN PATENT DOCUMENTS

FR  2587813 A  *  3/1987

OTHER PUBLICATIONS

Delback, FR2587813 Patent Translate Machine Translation, Mar. 27, 1987, European Patent Office.*

*Primary Examiner* — John Rivell
*Assistant Examiner* — Matthew W Jellett
(74) *Attorney, Agent, or Firm* — Svendsen Legal, LLC (57) ABSTRACT

A bladder system and apparatus for use with a beverage barrel or container, to reduce undesirable head-space in a wooden container of a beverage, especially a fermented beverage, such as wine. The system continuously protects the beverage contained in a wooden barrel from the harmful effects of oxidation at the air-to-fluid interface in the head-space and compensates for ullage, attributable to evaporation, leakage or sampling losses. The system includes an inflation stem connected to a barrel bladder inflatable by filling with an inflation gas. The inflation stem includes a liquid level sensor and inserts into a bung opening. The fluid level is sensed and a gas valve opens to fill the bladder, reducing head-space within the barrel. The system can combine the control of several barrels and optionally with other sensors, to create a barrel monitoring and control network.

11 Claims, 11 Drawing Sheets

BEVERAGE BARREL BLADDER SYSTEM AND APPARATUS

TECHNICAL FIELD

The invention relates to a bladder system and apparatus, especially suited for use with a beverage barrel, and more specifically for reducing undesirable head-space in a wooden container of a fermented beverage, especially wine. The bladder system continuously protects the beverage contained in a wooden barrel from the harmful effects of oxidation at the air-to-fluid interface in the head-space, and compensates for ullage, as often attributable to evaporation, leakage or sampling losses.

BACKGROUND OF THE INVENTION

The ageing process for red wine requires slowly evolving oxidation and reduction reactions over an extended period of time. There are many complex chemical reactions that occur in such a process, and it is important for these reactions to occur naturally at the interface of the surface of wine, in direct contact with wood, such as in a properly filled and coopered barrel. Wood is a semi-porous material, and therefore the quantity of wine within the barrel is reduced by the evaporation of constituent water and ethanol, through pores and joints in the wooden barrel. Subsequently, the volume of wine is naturally shrinking over time at a rate of approximately two to four liters per month, depending on several factors including, but not limited to, temperature, humidity, wood porosity, barrel construction, and the surface area of wine exposed to wood. As evaporative losses occur within a wooden barrel, a "head-space" develops within the barrel, above the wine, and leads to an ever-increasing air-fluid interface, where oxidation occurs that is considered undesirable. This undesirable oxidation not only accelerates the premature aging of wine by complex chemical reactions occurring at the air-fluid interface, but the presence of oxygen within the expanding head-space inevitably leads to microbial growth on the surface of the aging wine. This microbial growth contaminates the wine, promoting off-flavors and spoilage. In an appropriately filled barrel, in which the head-space volume is maintained at a minimum, such contamination is curtailed.

Historically, wooden barrels are the containers of choice in the winemaking industry for storing and aging wine for many reasons. Primarily, the wood imparts flavoring to the wine, and this flavoring varies with the type and quality of the wood. The amount of flavoring imparted to the wine is dependent on the size of the barrel and therefore, the ratio of wine to the inside surface area of the barrel. The age of the barrel is also important, along with the length of time the wine is stored within it. Standard wine barrels are coopered from white oak, and generally contain only about sixty gallons, which is very small, considering the large, industrial constrainments and tanks employed for other beverage processing.

The typical flavor imparting life-span of the standard oak barrel employed in winemaking is considered to be approximately three years. However, more that fifty-percent of the oak's available flavoring is extracted into the wine within the first twelve months of use. Additionally, many wineries employ the use of "neutral" oak barrels, which have been used for more than three years to continue storing some wines, and no longer impart any significant flavors to the wine. Barrel selection depends on the wine varietal, the winemaker's choice and the financial resources of the winery, as the average price for each oak barrel typically exceeds several hundred U.S. dollars.

There are several other reasons oak barrels remain in use today, either in new or neutral condition. As discussed above, slow and desirable oxidation and reduction reactions occur over time, as wine evaporates through the natural pores of the wooden barrel staves and oxygen permeates back through the wood. This slow oxidation is not only desirable but is considered mandatory for creating premium wines. Despite the drawback of creating the aforementioned head space, the desirable oxidation occurring at the interface of wood and wine is considered vital to the production of premium wine.

The term "ullage" is used to describe the loss or leakage of wine from its container. The natural evaporation or loss of wine through the barrel is supplemented by leakage and sampling. In an attempt to control ullage, wineries devote large sums of money to create and operate elaborate humidification systems, and for the labor required to consistently "top-up" the barrels, to minimize head-space. Additionally, the "top-up" wine is often inferior quality, newer wine, which detracts from the flavor of the aged wine within the barrel. However, even the most diligent topping-up fails to eliminate ullage, and the undesirable favoring resulting from head-space oxidation. This effect is magnified, especially when pushing for larger numbers of barrels, as necessary for wineries to achieve an advantage in economic scale of production.

Oak barrels posses other characteristics that ensure their ongoing use in modern-era winemaking, including the natural antiseptic qualities of wood, and the near-absence of electrostatic charges of wood particles. In containers made of stainless steel, for instance, there is a natural stratification or "layering" effect that occurs during wine settling, due to the electrostatic characteristics of metal, which typically mandates filtration for clarification. In addition, the charring of the wooden barrel staves, as typically achieved during "fire-bending" in the coopering process, leads to a slow and natural, charcoal adsorption of impurities from the stored wine.

Therefore, smaller oak barrels are the time-tested container of choice for storing and aging premium wines. However, a system is needed to improve the performance of wood barrels, especially in lager scale wine making operations, still employing the smaller oak barrels. There is a need for more consistent and cost-effective techniques for minimizing head-space in aging barrels, and prevent dilution effects attributable to topping-up, and assure better and more consistent quality in the production of wine.

The following is a disclosure of the present invention that will be understood by reference to the following detailed description taken in conjunction with the accompanying drawings.

Reference characters included in the above drawings indicate corresponding parts throughout the several views, as discussed herein. The description herein illustrates one preferred embodiment of the invention, in one form, and the description herein is not to be construed as limiting the scope of the invention in any manner. It should be understood that the above listed figures are not necessarily to scale and that the embodiments are sometimes illustrated by fragmentary views, graphic symbols, diagrammatic or schematic representations, and phantom lines. Details that are not necessary for an understanding of the present invention by one skilled in the technology of the invention, or render other details difficult to perceive, may have been omitted.

DETAILED DESCRIPTION OF SPECIFIC EMBODIMENTS

The present invention provides a bladder system and apparatus, able to reduce a head space in a wooden container of a fermented beverage, especially wine. When employed in the wine making process, the bladder system and apparatus continuously protects the aging wine contained in a wooden barrel from the harmful effects of oxidation at the air-to-fluid interface and also compensates for the loss or leakage of wine from its container, referred to as "ullage," which is often attributable to evaporation, leakage or wine sampling losses.

FIGS. 1 through 8 show preferred embodiments and features of the bladder system and apparatus 15, or simply referred to herein as the bladder system. The bladder system is configured to monitor and react to the quantity of a fermented beverage, which can generally be referred to herein as a beverage 17, such as wine, cider, juice or spirit, as stored within a container that is preferably made primarily of wood, such as a barrel 18. The bladder system includes a barrel service mechanism 20, as shown inserted into the barrel, in FIGS. 1 and 2. The barrel service mechanism has an inflation stem 21 connected to an inflatable bladder 22.

Figure 1:
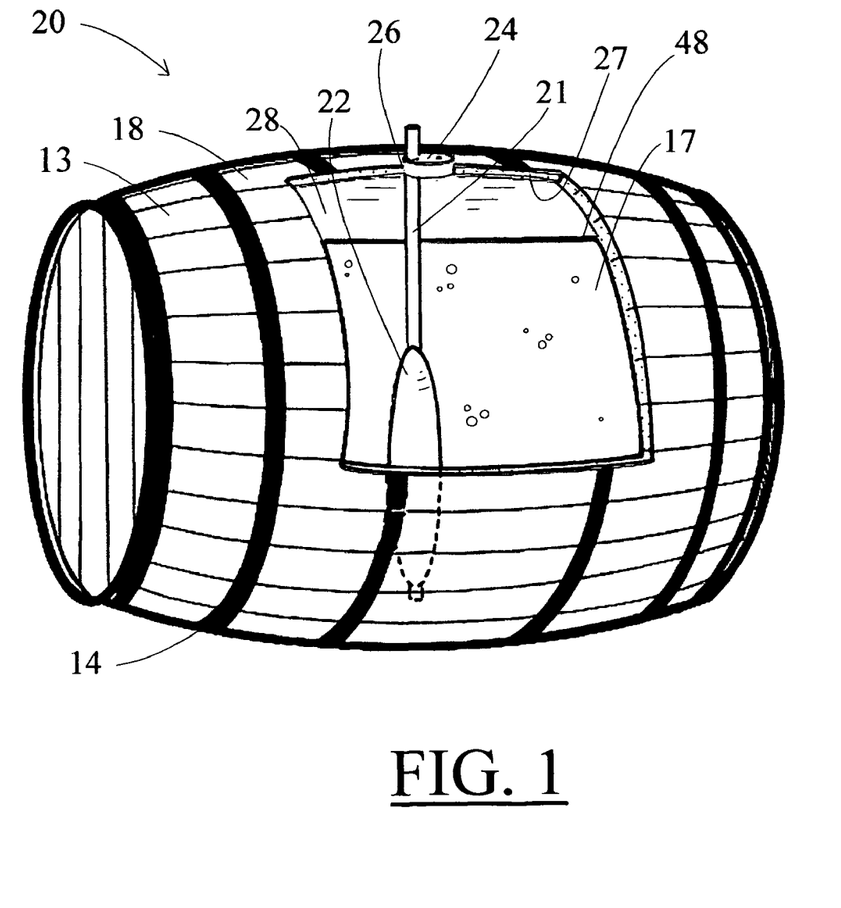
FIG. 1 is a partially sectioned perspective view of a portion of a barrel bladder system, according to an embodiment of the invention.
Figure 2:
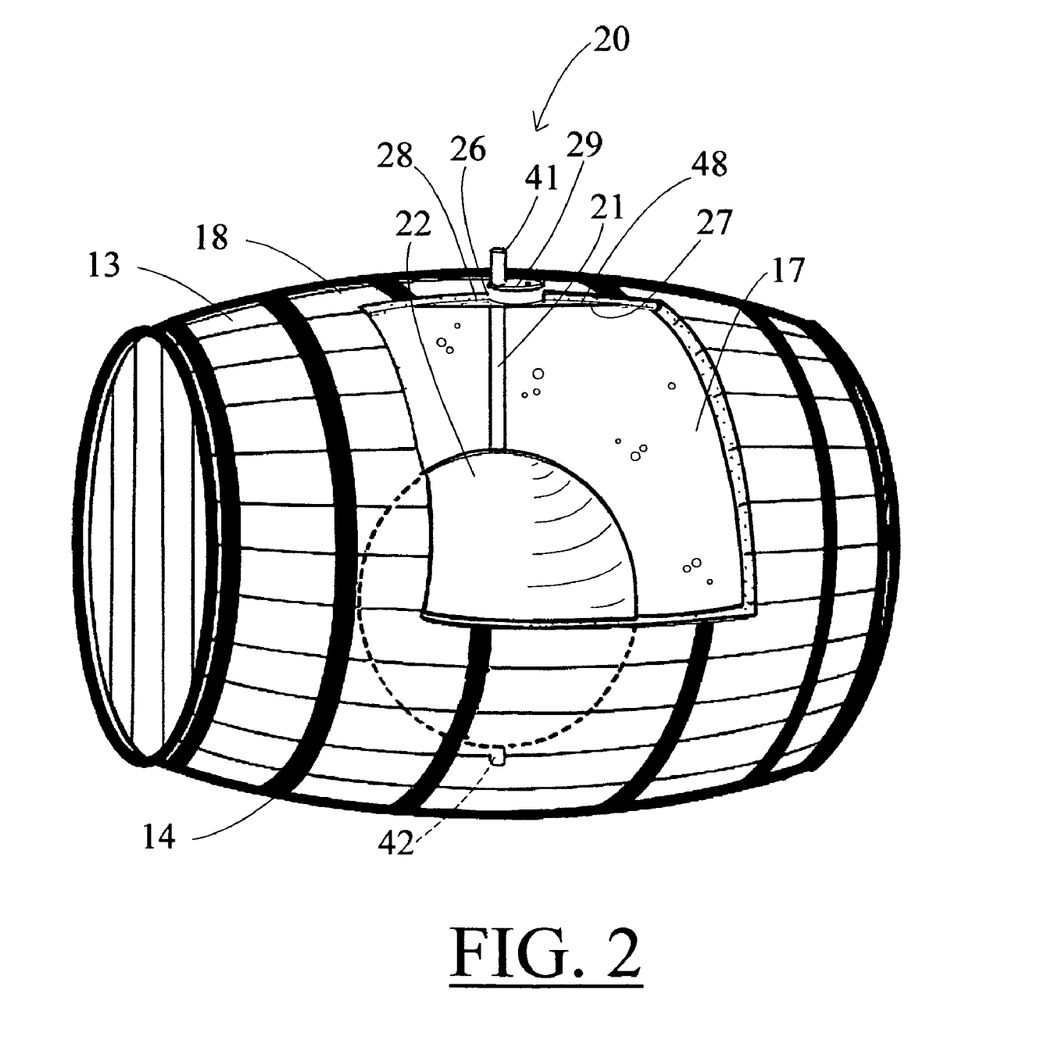
FIG. 2 is a partially sectioned perspective view of a portion of a barrel bladder system, according to an embodiment of the invention.

The barrel 18 can be any conventional container, typically formed of wood staves 13 held together with metal bands or "hoops" 14, as employed for storing wine, or any other beverage 17, such as beer, cider, juice, brandy, whiskey, or more generally spirits, or any other beverage that may be fermented, as known to those skilled in the crafting of such beverages. Standard wine barrels are coopered with staves of white oak, and can generally contain approximately sixty gallons. The bladder 22 and inflation stem 21 are insert-able into the barrel when the bladder is uninflated, as shown in FIG. 1. The uninflated bladder and attached inflation stem can be inserted through and anchored within a bung opening 26 of the barrel. Typically, the barrel can be rolled to place the bung opening proximate to an upper container surface 27 of the barrel, which is the high point of the barrel when the barrel is placed on its side, as shown in FIGS. 1 and 2. A "head-space" 28 is typically found in the barrel, as shown in the barrel's cutaway area of FIGS. 1 and 2. The head space is a pocket of air or gas, formed above the beverage within the barrel, also proximate to the high point of the barrel.

The inflation stem 21 is received into an inflation stem housing 29, which includes a bung anchor 31. The bung anchor acts as stopper, and is inserted into the bung opening 26 of the barrel, typically with a threaded attachment, to anchor within and seal the bung opening, while allowing the passage of elements of the barrel service mechanism 20, as needed and further disclosed herein.

As shown in FIGS. 4A through 4D, the inflation stem housing 29 of the barrel service mechanism 20 also holds a liquid level sensor 33. The liquid level sensor can be any conventional sensor with the ability to detect the level of a liquid, and output, modify or modulate a signal, based upon the sensed level. The liquid level sensor may be mounted within the head space 28 of the barrel 18, as preferred, or it may be substantially external to the barrel and detect the liquid level 48 through the container, as with ultrasonic pulses. The liquid level sensor may be analog or digital in nature, and may simply be a normally open, as preferred, or a normally closed float switch. Float switches are well known in technologies requiring liquid level sensing. A standard, electro-mechanical analog float switch, which maintains an open circuit in its normal operational mode is preferred, and may be coupled with a temperature sensor or any other sensor desired, such as dissolved oxygen and dissolved carbon dioxide, as options. Alternately, a solid state fluid level sensor, such as an optical level sensor can be utilized as the liquid level sensor, as discussed further herein.

Figure 4A:
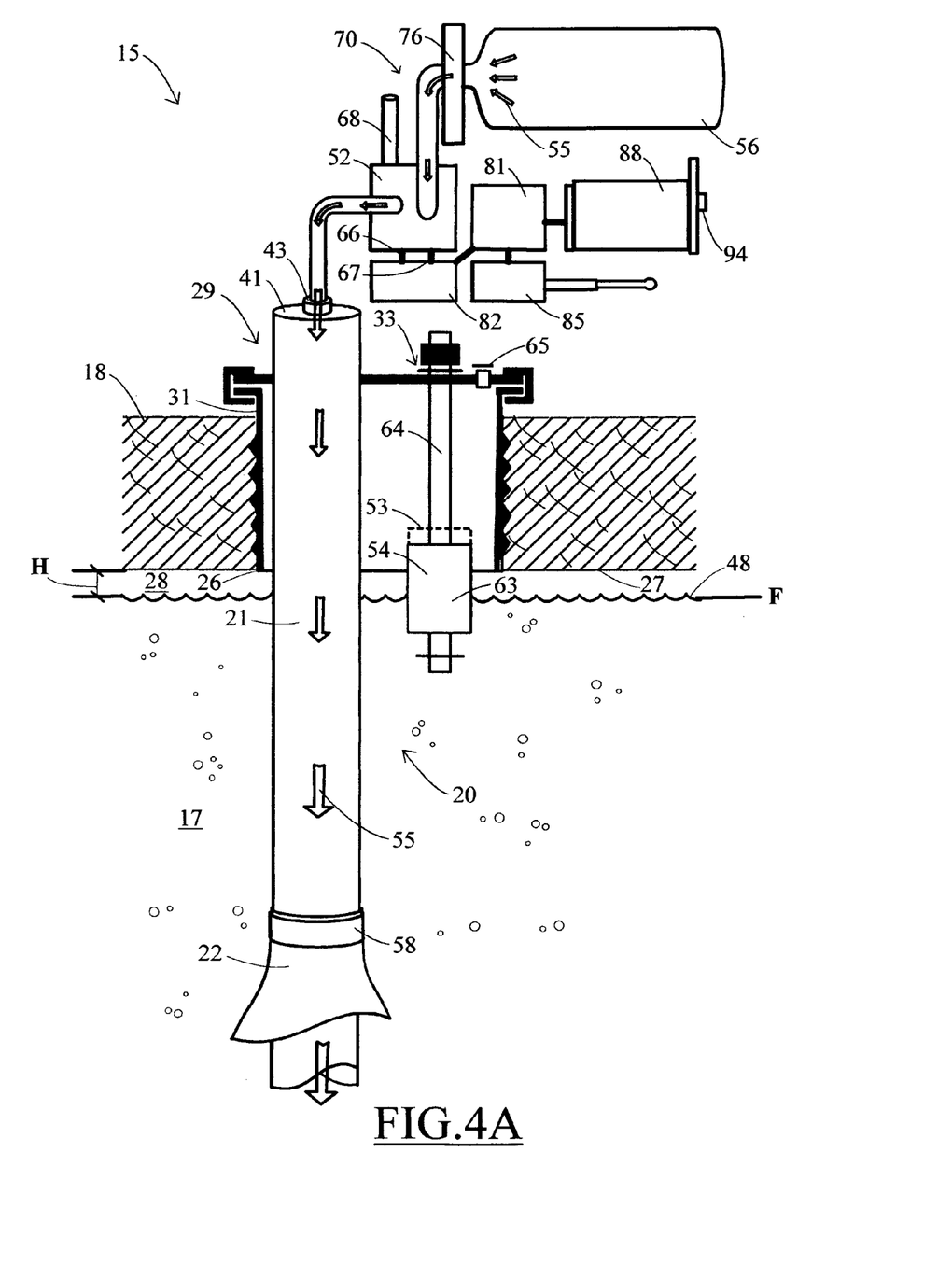
FIG. 4A is a partially sectioned side view of a portion of a barrel bladder system, according to an embodiment of the invention.

The inflation stem 21, preferably anchored vertically within the inflation stem housing 29, includes an upper stem end 41 and a lower stem end 42, as shown in FIG. 4A, with an inflation port 43 located proximate to the upper stem end, and a bladder port 44, which is located proximate to the lower stem end. Preferably, the inflation stem is manufactured from a stainless steel alloy, or some such material that will not corrode or impart any taste or flavor to the beverage 17 within the barrel 18. The liquid level sensor 33 is able to detect a liquid level 48, within the head-space 28 of the barrel. By sensing the liquid level, in "approximate" relation to the upper container surface 27, a head height "H" is determined. The terms "approximately" or "approximate" are employed herein throughout, including this detailed description and the attached claims, with the understanding that is denotes a level of exactitude commensurate with the skill and precision typical for the particular field of endeavor, as applicable.

Figure 4B:
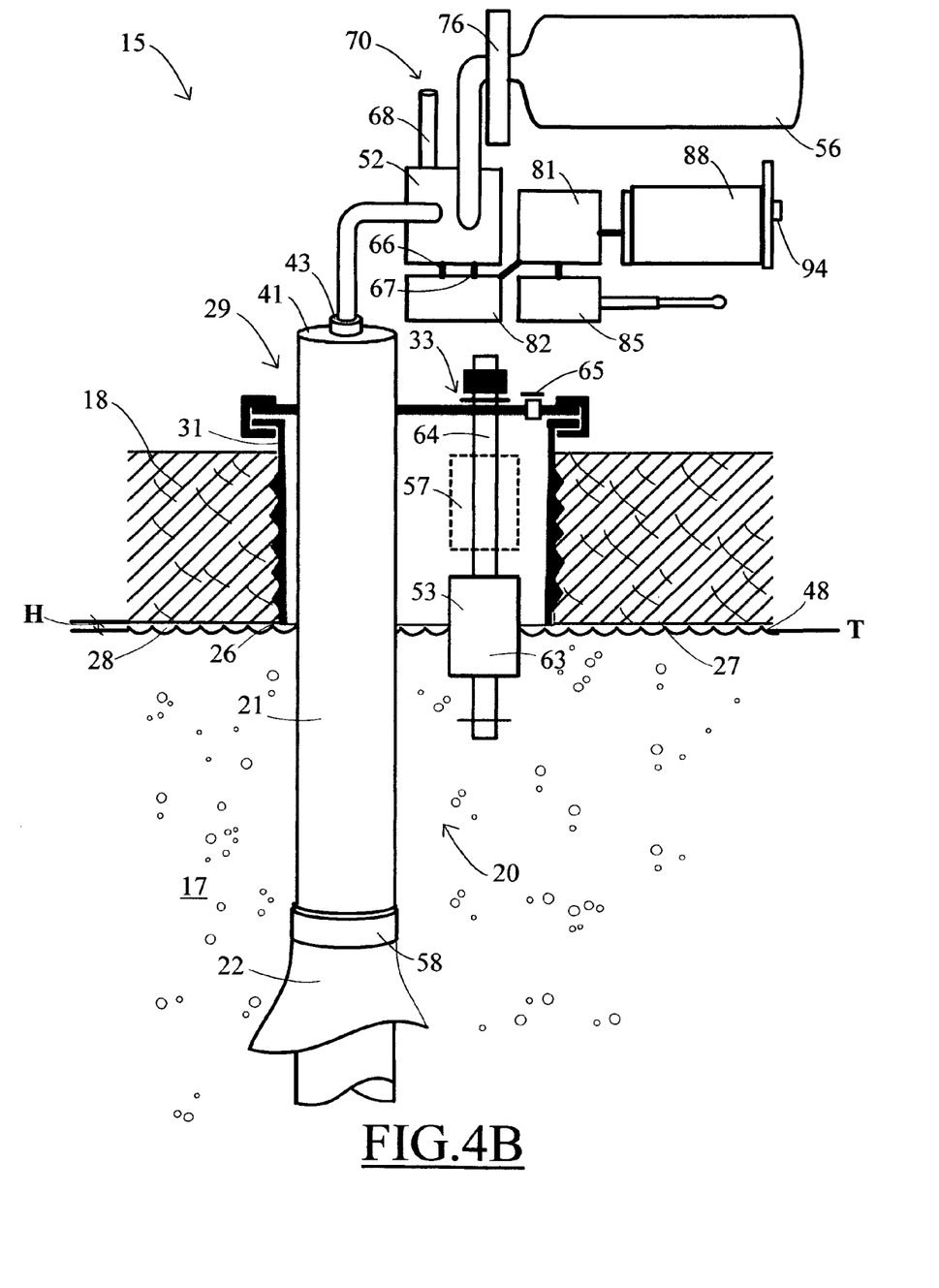
FIG. 4B is a partially sectioned side view of a portion of a barrel bladder system, according to an embodiment of the invention.
Figure 4C:
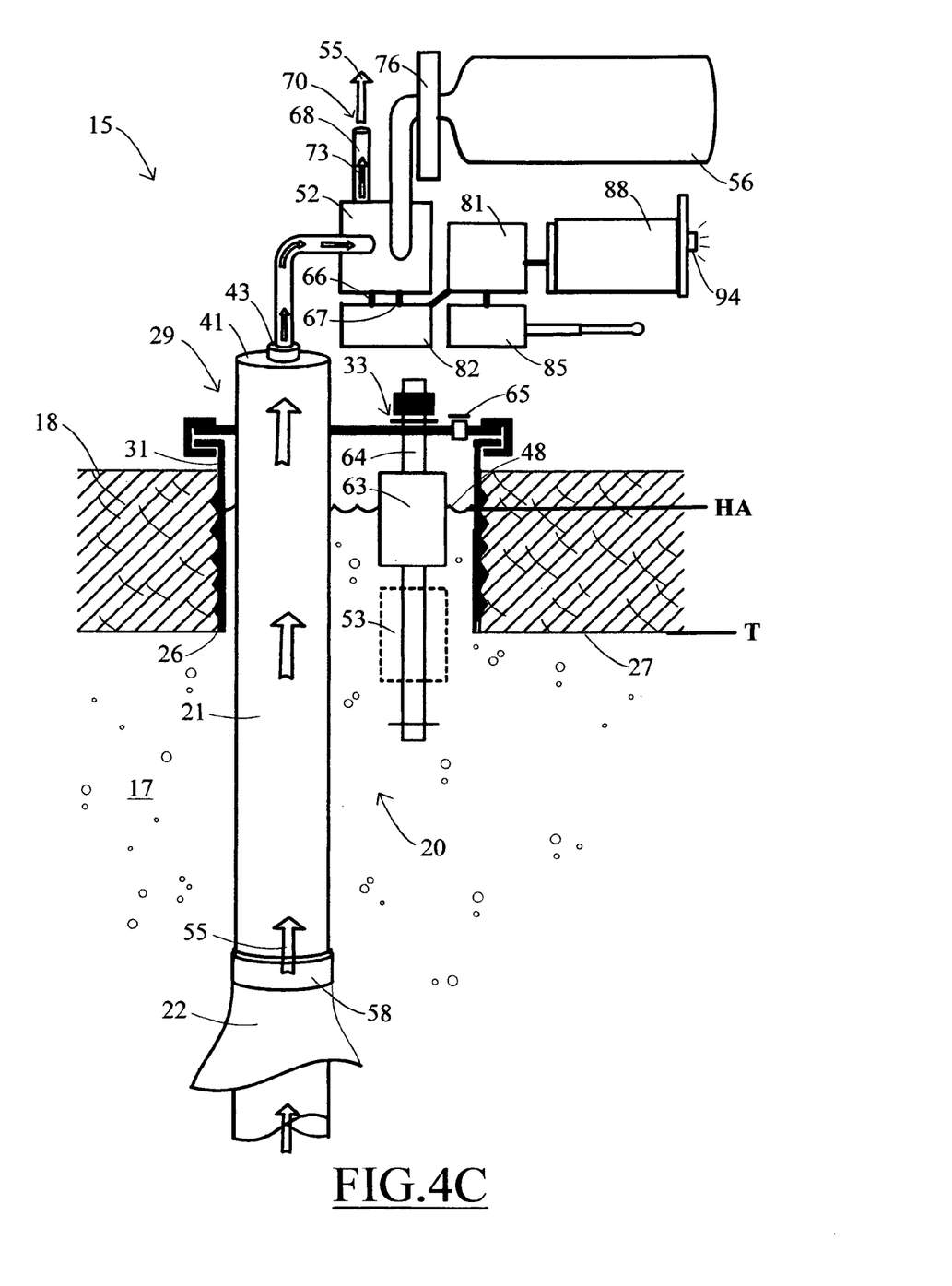
FIG. 4C is a partially sectioned side view of a portion of a barrel bladder system, according to an embodiment of the invention.
Figure 4D:
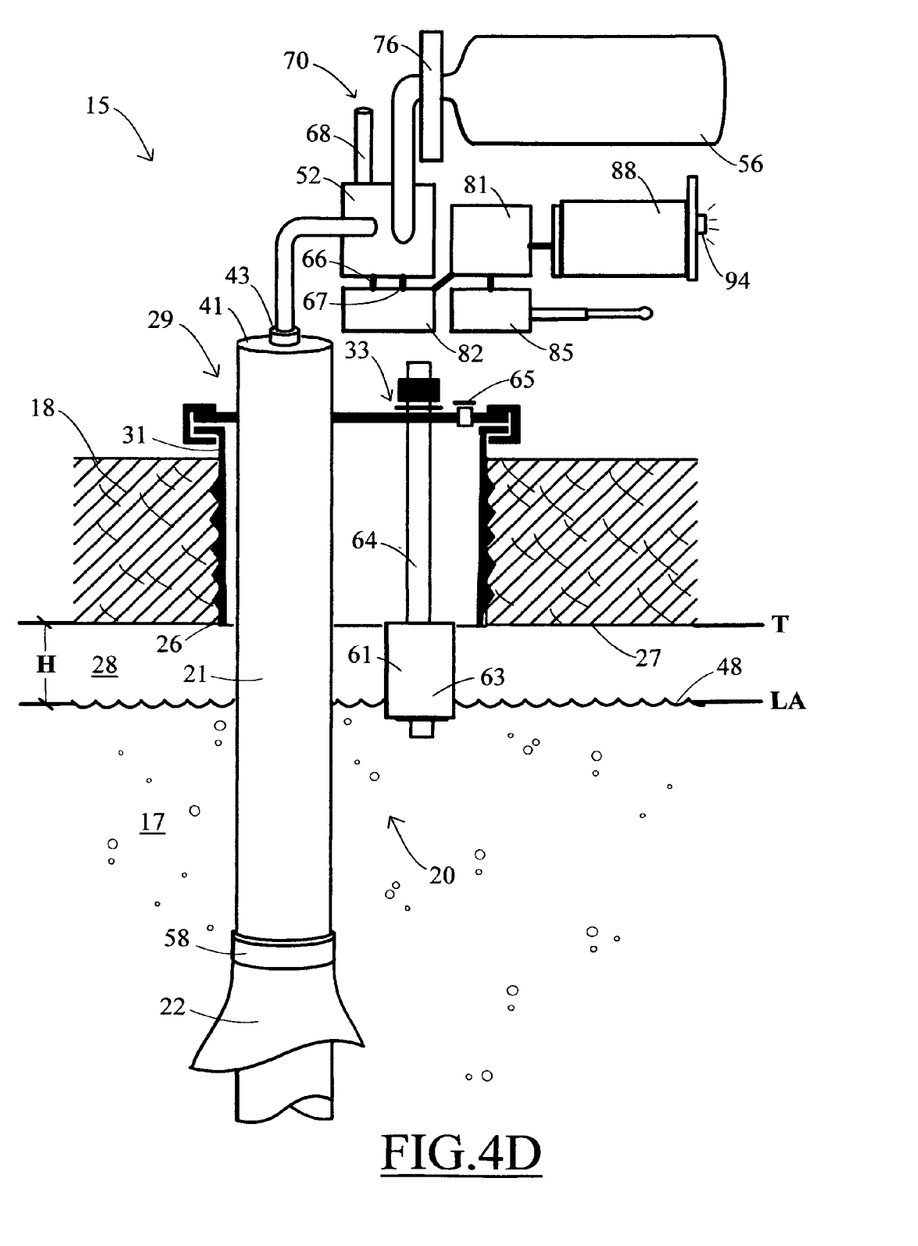
FIG. 4D is a partially sectioned side view of a portion of a barrel bladder system, according to an embodiment of the invention.

The head height H is herein defined as a vertical distance between the upper container surface proximate to the bung opening 26, and the liquid level 48, directly beneath the bung opening. FIGS. 4A, 4B and 4D show various head heights in different operational scenarios or modes, of the bladder system 15. The head height is reduced by filling the bladder 22, which is inflatable by filling with an inflation gas 55, which is stored in a gas tank 56 also referred to herein as a gas container. A gas valve 52 opens as directed, when a signal to inflate the bladder is initiated by the liquid level sensor 33. When the gas valve opens, the inflation gas is released from the gas tank, and routed to the inflation stem 21 of the bladder service mechanism 20.

In a preferred operation of the bladder system 15, as shown in FIG. 4A, the liquid level sensor 33 includes a float 63 that travels along a reed 64. Most preferably, the liquid level sensor acts as a switch, to close a gas valve circuit 66, when the liquid level 48 falls below a preset, low or fill level "F," as shown in FIG. 4A. The gas valve circuit is most preferably a low voltage control circuit, with the gas valve normally closed in the non-energized state, or equivalently acting sensor and circuit, as are known to those skilled in industrial system control and design.

As the volume of wine 17 within the barrel 18 decreases over time, the float 63 of the liquid level sensor 33 lowers from a target position 53 to a fill position 54, as shown in FIG. 4A, which results in the sending of an "open valve" signal to the gas valve 52, preferably by initiating closing of the gas valve circuit 66 to open the gas valve, as discussed above. This open valve signal occurs when the head height H is greater than a predetermined low level, referred to herein as an inflate or fill level "F". The fill level is the low end of the normally fluctuating liquid level 48 of the wine or beverage, within the barrel.

Figure 3:
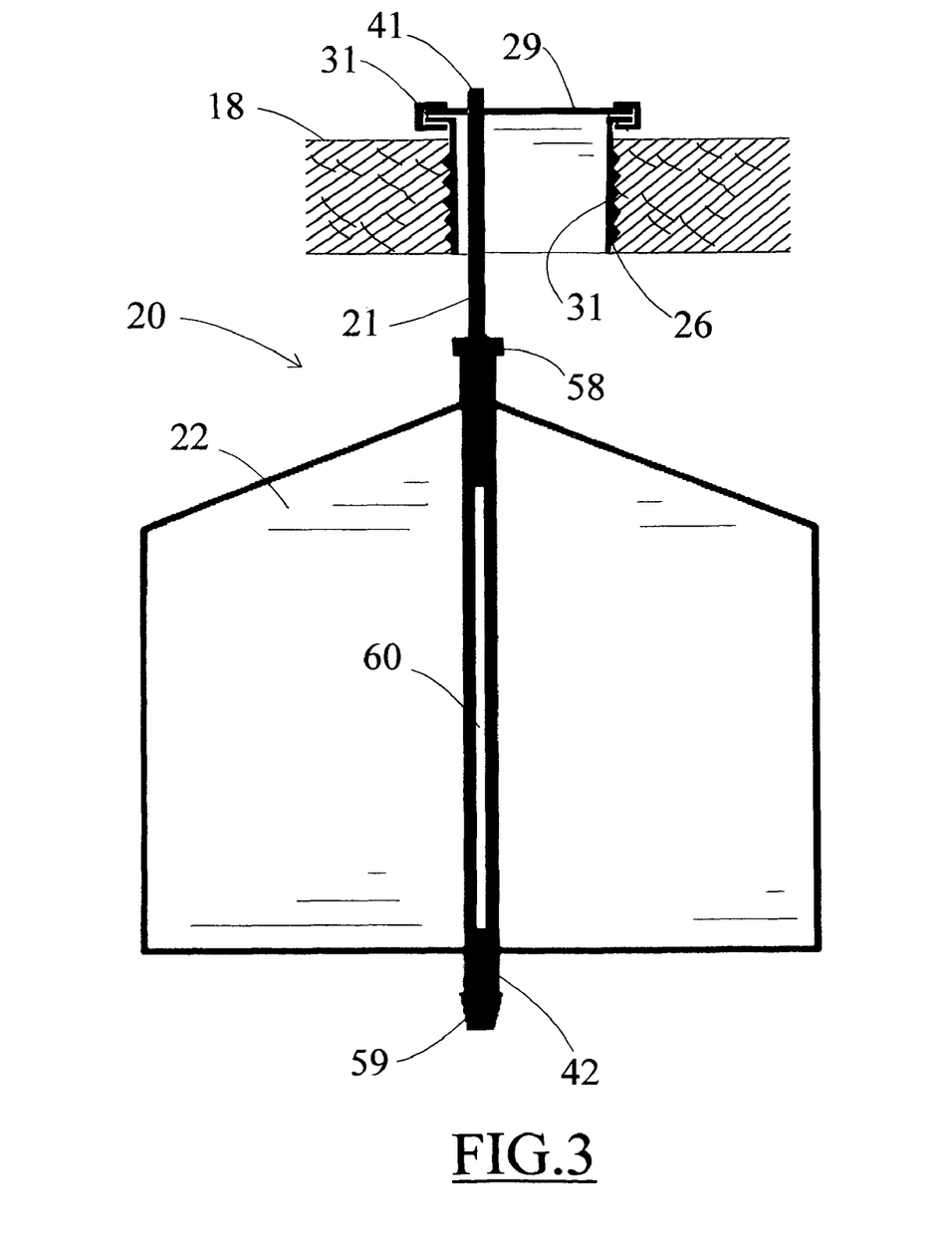
FIG. 3 is a partially sectioned side view of a portion of a barrel bladder system, according to an embodiment of the invention.

The bladder 22 is inflated while it is submerged within the barrel 18 during action of the pressurized feed of the inflation gas 55, as metered through the gas valve 52. The forced introduction of the inflation gas into the bladder inflates the bladder to displace the beverage 17 into the volume of the head-space 28, by raising the liquid level 48 within the barrel, and so reducing the head height H. The bladder is most preferably a thin walled rubber, or other semi-elastomeric, synthetic and substantially non-permeable and rubber-like material, such as a poly propylene, and shaped as shown in FIG. 1 or alternatively in FIG. 3. The material is selected to undergo repeated stress on inflation, and also to exhibit little or no diffusion, and be unreactive with the beverage 17 contacted within the barrel, or with the inflation gas. A preferred size of the bladder is approximately ten percent of the volume of the barrel. For a standard sixty gallon barrel, a preferred bladder is approximately three to ten gallons in volume, with a most preferred size of five gallons. As shown in FIG. 3, the bladder is affixed to the inflation stem 21. The bladder is slipped over the distal part of the stainless steel shaft of the inflation stem housing, like a sleeve, and will slide under an anchor ring 58, preferably with an airtight, silicon seal. At the lower stem end 42, a bottom anchor 59 is preferably employed, also with an airtight seal. The bottom anchor attaches snugly, preferably with a threaded connection, to secure the bottom end of the bladder to the inflation stem. Also, the inflation stem includes a gas slot 60, along the inflation stem within the bladder.

The inflation gas 55 can be any gas that is preferably inert and will not add off-flavoring or react with the beverage 17 stored within the barrel 18. A most preferred inflation gas is carbon dioxide, or alternatively argon or nitrogen.

The bladder system 15 is shown in FIG. 4B with the float 63 of the liquid level sensor 33 in its target position 53 and the liquid level 48 in a targeted, or "target" position "T," with the head height H, minimized to be as near as practicable to the upper container surface 27. As the bladder system responds to the filling of the bladder, and the float 63 rises along the reed 64, from the fill position 54 back to the target position 53, as shown in FIG. 4A, the gas valve circuit reopens to shut off the filling of the bladder and maintain the liquid level at the targeted position T, shown in FIG. 4B, with excess gas in the head-space 28 relieved from the inflation stem housing 29, through bung relief port 65, shown in FIGS. 4A through 4D, 5 and 6.

Additionally, the bladder system 15 preferably includes critical alarm monitoring, to verify proper operation of the system. As shown in FIG. 4B, the float 63 of the liquid level sensor 33 may rise from the target position 53 to a high alarm position 57. As further shown in FIG. 4C, if the liquid level 48 rises well above the target level T, to a high alarm level "HA," the float also rises to the high alarm position, preferably causing a high alarm circuit 67 to close. Activation of the high alarm circuit serves to open a relief port 68, which is preferably a component of the gas valve 52. The high alarm circuit is most preferably a low voltage control circuit, as is known to those skilled in industrial system control and design. As the bladder system responds to the release of the inflation gas 55 from the relief port, as shown in FIG. 4C, the bladder deflates, and the float lowers along the reed, back to the T position as shown in FIG. 4B, and the high alarm circuit reopens to shut off the release of inflation gas through the relief port, and continue to maintain the liquid level at the targeted position T. The closing of the high alarm circuit can also serve to activate an alarm, to notify the operator of a possible overfill of the barrel 18, or overinflation problem with the bladder 22.

Most preferably, as shown in FIG. 4D, the reed 64 of the liquid level sensor 33 extends below the fill level "F," to a low alarm level "LA." This allows the float to drop to a low alarm level 61, which preferably closes a low alarm circuit, and opens the gas valve circuit to close the gas valve, preventing the possible overinflation and rupture of the bladder 22, or waste of the inflation gas 55 due to leak or malfunction. The closing of the low alarm circuit can also serve to activate an alarm, to notify the operator of the under-fill of the barrel 18, or a near maximum inflation of the bladder.

Figure 5:
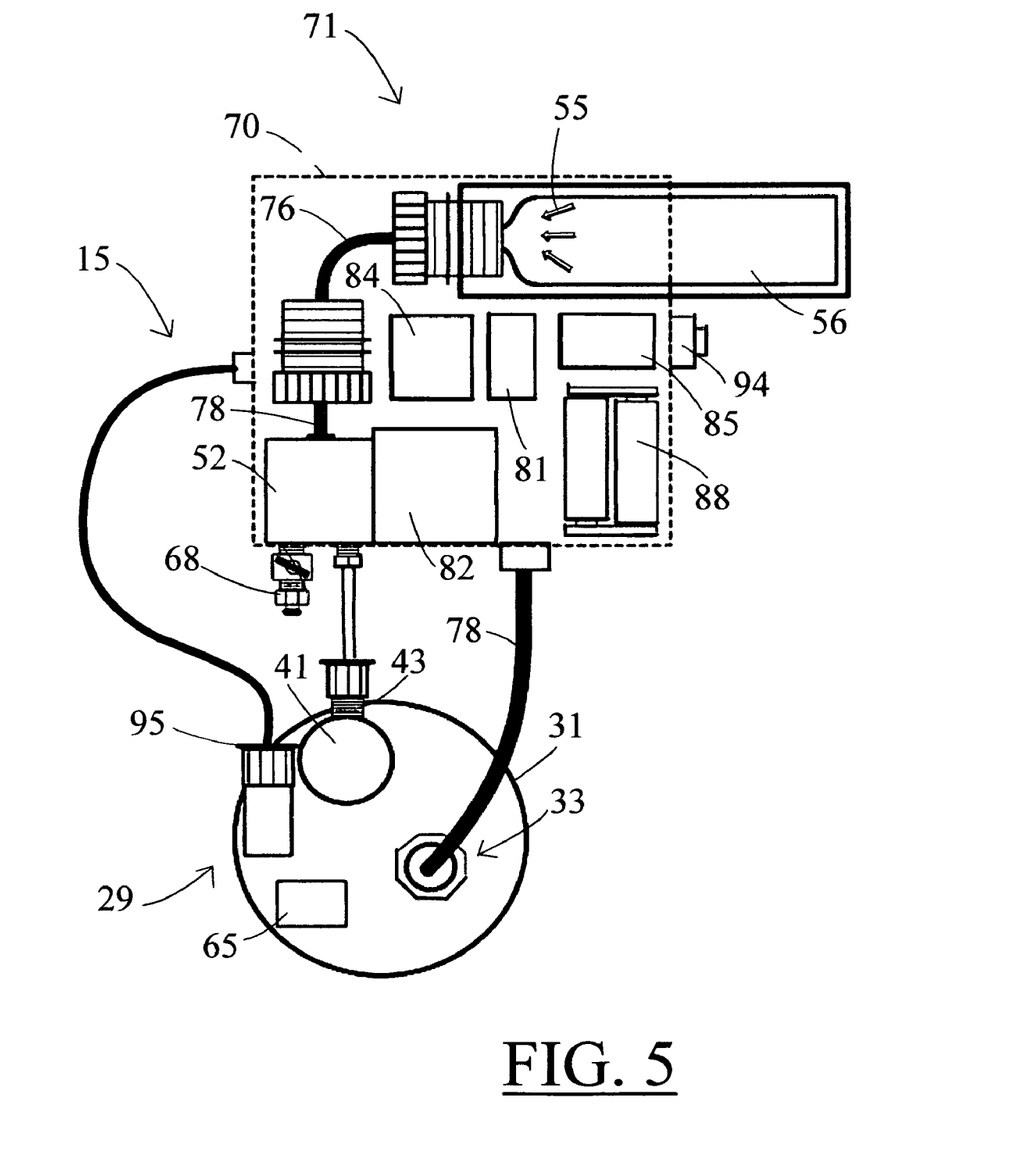
FIG. 5 is a top view of a portion of a barrel bladder system, according to an embodiment of the invention.

A key component of the bladder system 15 is a control module 70, as shown in FIG. 5. The control module connects and communicates directly with the barrel service mechanism 20, which is inserted into each barrel 18, as discussed above. The control module regulates the feed of the inflation gas 55 into the inflation stem 21, as a result of the electronic feedback from the liquid level sensor 33. Additionally, as shown schematically in FIG. 7, the control module preferably includes the ability to communicate to a local server 74, for tracking operational activity of the control module, and to incorporate a multiple of control modules into a control network 75, as detailed later, herein.

The control module 70 includes the gas valve 52 for controlling the flow of the inflation gas 55 into the inflation stem 21 of the barrel service mechanism 20. The gas valve is activated in response from changes in the liquid level 48, as sensed by the liquid level sensor 33. The inflation gas 55 is supplied to the actuator valve from the gas container 56, which is preferably a tank of the inflation gas, pressurized or alternatively liquified within the container. A central, large gas container may serve any multiple of barrels 18, simply manifolded though a gas pressure regulator 76, and routed through a gas line 78 to the gas valve 52 of each control module 70, as needed for inflation of the individual bladders 22. Smaller, easily managed gas containers are preferred, which minimize hazards of handling pressurized gas tanks or containers, especially during transport.

Figure 6:
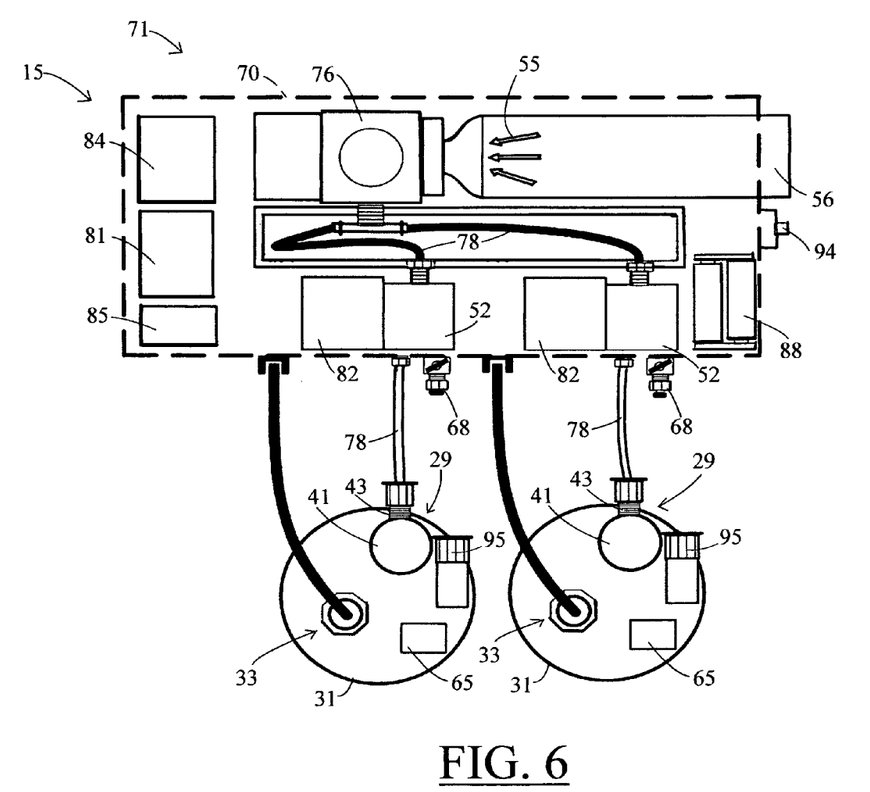
FIG. 6 is a top view of a portion of a barrel bladder system, according to an embodiment of the invention.
Figure 7:
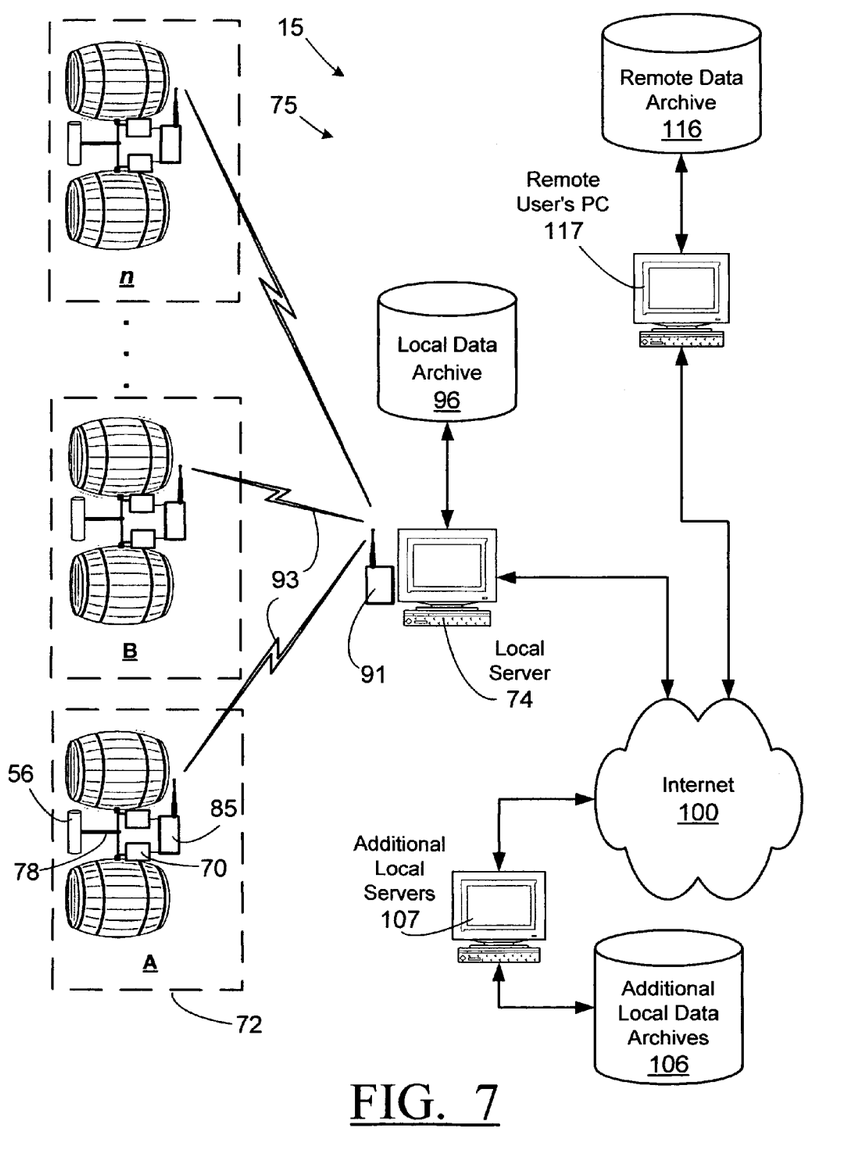
FIG. 7 is a schematic view of a networked barrel bladder system, according to an embodiment of the invention.

Preferably, the gas container 56 may be embodied by a single tank of supply inflation gas dedicated to each barrel 18, in a single barrel set-up 71, as shown in FIG. 5, or the gas container may be coupled in a duplex barrel set-up 72, as most preferred, with a dedicated gas infeed line 78, to the gas valve 52 of each control module 70, as shown in FIGS. 6 and 7. The control module's operation of the gas valve is preferably accomplished with a logic module 81 and a controller 82, as shown schematically in FIG. 8. The controller can be any electro-mechanical valve controller, such as a solenoid, and the logic module preferably includes an onboard memory 83, interfaced with a control microprocessor 84, the design and operation of which are well known to those in the field of remote controlled firmware for small valves. The onboard memory storage is preferably a conventional "flash" type of memory device that stores the computing instruction or the controller, along with and any collected operation data, for transmission to the local server 74. Additionally, a digital-to-analog conversion module 87 can also be included within the logic module, to actuate and monitor the controller with instructions based upon digital signals. The digital-to-analog conversion module can be utilized for any needed conversions of digital instruction to analog outputs from the control module, or the analog-to-digital conversion of analog information input to the control module.

Most preferably, the control module 70 is powered with low voltage circuitry, which can be supplied by a low voltage electrical supply connection, or more preferably by a battery 88. The battery is most preferably continually recharged, to prevent interruptions in power to the control module.

Figure 8:
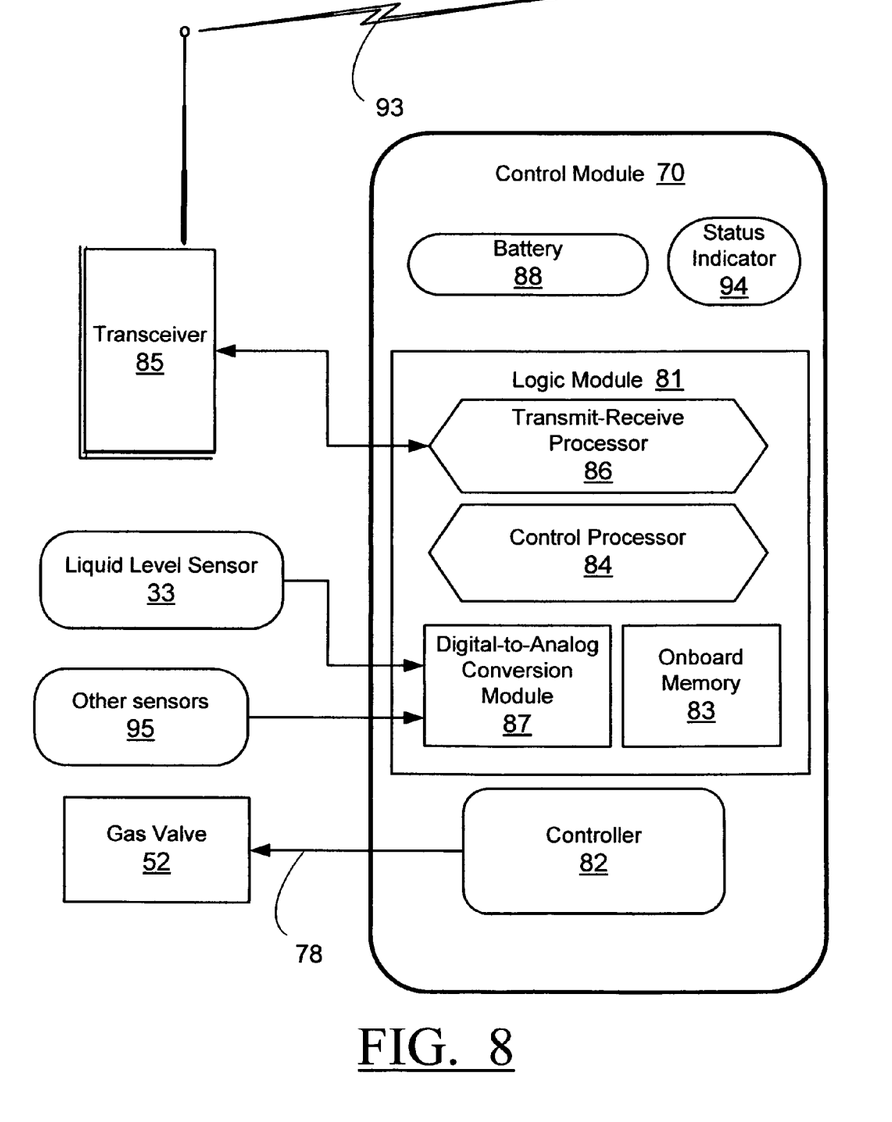
FIG. 8 is a schematic view of a networked barrel bladder system, according to an embodiment of the invention.

Additionally, especially in the preferred, control network 75 embodiment of the bladder system 15 as shown in FIGS. 7 and 8, a transceiver 85 is included within or in close proximity to the control module 70. With conventional digital wireless transmission and receiving circuitry, the solid state transceiver preferably receives direction from a transmit-receive processor 86, as shown in FIG. 8, which directs the timing format of sent and received sequences of fixed-length digital data to a router 91, which is a component of the local server 74, and preferably able to receive and transmit to the individual control modules through each transceiver.

Through the router 91, the local server 74 has the ability to oversee and direct the operation of several control modules 70 by communications through the router. Each transmit-receive processor 86 can perform conventional data-logging functions to regularly transmit the operational status or sensor inputs, as temporally stored in the onboard memory 83 of the logic module 81.

The transceiver 85 of the control module 70 can communicate with the router 91 by a wired connection, or a wireless connection, as preferred. The transceiver may emit or receive a communication signal 93, to or from the router. The communication signal is preferably a local-area type of transmission, with a unique digital identification to any specific control module that it emanates from, or is directed to. The frequency band of the communication signal may be any conventional communication band, such as infrared, radio, or alternatively in higher frequencies, as employed by Bluetooth™ transceivers. Conventional "polling" routines may be employed by the local server 74 to verify communication linkage to and proper operation of the control modules. The local server thereby is alerted when any of the control modules fail to respond, such as in a board failure or loss of power.

As an additional feature for each control module 70, a status indicator 94, such as a conventional LED can be employed, as shown in FIGS. 4A through 4D, 5, 6 and 8, to visually display the operational condition of the bladder system, as sensed by the control module, such as "nominal operation," or "alarm." Audible alarms can also be included with or instead of the LED as a status indicator.

Importantly, additional or other sensors 95 may be incorporated within or external to the barrel service mechanism 20 for each control module 70, if desired. This allows the barrel service mechanism to act as a sensor platform. Examples of additional sensors include ambient temperature, beverage temperature, sugar or 'Brix' level metering, pH, gas composition, or any other conventional chemistry probes, as desired to be telemetered in conjunction with the operation of the bladder system 15.

Additionally, the inflation stem housing 29 can be separate from the barrel service mechanism or the additional sensors 95. For instance, the inflation stem 21 and attached bladder 22, could be inserted into a second bung opening at the side, the bottom, or at the head of the barrel 22, if convenient or desired.

Most preferably, calculation of and tracking of the volume of wine 17 lost from the barrel 18 as a function of the pressure of the inflation gas 55 with the bladder 22 is performed, or alternatively approximated by the time of solenoid valve opening and feed pressure of inflation gas 55. This additional sensed information can be included in the information processed by the logic module 81 and stored in the onboard memory 83 of the control module, and telemetered to the router 91 and local server 74, with aid of the transmit-receive processor 86, thus creating an 'intelligent' barrel sensing and control network.

As shown in FIG. 7, any realistic multiple of control modules 70 may be included in the control network 75, designated as "A," along with "B," and up to "n" control modules, all networked into the local server 74 through the router 91. Preferably, the local server includes a "local data archive" 96, that collects operational data, as polled from the networked control modules, over time. By way of a standard connection to the Internet 100, this data may be shared or augmented with "additional local data archives" 106, as collected by additional servers 107, each overseeing the operation of control modules in other bladder systems 15.

As an additional and significant feature, a central, "remote data archive" 116 could be stored at a remote user's PC 117, to collect, compile and analyze the operational data from several bladder systems 15. This data and interface with a multiple of networked bladder systems forms the overarching control network 80, which can be employed to optimize the operation of the individual bladder systems.

Also, the information collected and analyzed by the control network 80 can include any additional parameter collected by the individual control modules 70 in connection to their barrel service mechanisms 20, or related sensors as previously described, herein.

The bladder system 15 of the present invention can be used by any winery that employs wooden barrels to store or age the wine 17 in the winemaking processes. The bladder system continuously protects the aging wine from the harmful effects of oxidation at the air-to-fluid interface, within the barrel 22, resulting from the conventional ullage processes. "Ullage" can be defined as the amount of wine lost from a barrel through natural evaporation, leakage or sampling. By maintaining the liquid level 48 at a high level during the aging or storage, and by directly replacing the volume of beverage, such as wine 17, which is lost with the inflation gas 55, injected into the bladder 22 has several unique and distinct advantages.

Importantly, the overall quality of the wine 17 is improved with use of the bladder system 15, by curtailing oxidation of the wine 17 at the head-space 28, as compared to conventional, manual "topping-up protocols," which depend on the manual inspection and filling of each barrel 18 in a preset schedule. This common protocol inherently causes an extended length of time to lapse between successive re-fillings of the barrel, and therefore allows an ever-enlarging surface area at the air-fluid level within the barrel, due to ullage. Oxidation, which is well known to be the principal spoiler of wine, is significantly reduced during barrel aging using the bladder system 15, by maintaining a near constant air-fluid level over time. Barrels of wine manually topped-up using standard techniques are usually filled with inferior quality wine called "top-up wine." This top-up wine is usually pooled from excess sources and it often comprises different varietals of wine, and is usually stored in small stainless steel containers limiting appropriate aging. In contrast, wine that is stored and aged using the bladder system requires very minimal, if any, dilution with different and inferior wine.

Additionally, the bladder system 15 provides for the safe and accurate quantifying of ullage, eliminating or greatly reducing the need for topping-off, making the process more efficient and safer to synchronize the consolidation of wines from the same or similar lots, if desired. Additionally, the bladder system reduces the personnel required and associated potentials for injury in traditional topping up methods, while improving the overall quality of wines produced with aid of the system.

In compliance with the statutes, the invention has been described in language more or less specific as to structural features and process steps. While this invention is susceptible to embodiment in different forms, the specification illustrates preferred embodiments of the invention with the understanding that the present disclosure is to be considered an exemplification of the principles of the invention, and the disclosure is not intended to limit the invention to the particular embodiments described. Those with ordinary skill in the art will appreciate that other embodiments and variations of the invention are possible, which employ the same inventive concepts as described above. Therefore, the invention is not to be The following is claimed:

1. A bladder system for reducing a head space in a container of a beverage, the bladder system comprising:
    an inflation stem connected to a barrel bladder, the barrel bladder inflatable by filling with an inflation gas;
    the inflation stem inserted into a bung opening of a wooden container, the wooden container having an upper container surface, and the bung opening located on the upper container surface of the wooden container;
    an inflation stem housing;
    the inflation stem received into the inflation stem housing,
    the inflation stem housing including a bung anchor, the bung anchor inserted into the bung opening of the wooden container, to seal the bung opening;
    the inflation stem including an upper stem end and a lower stem end;
    an inflation port proximate to the upper stem end;
    a bladder port proximate to the lower stem end;
    a liquid level sensor mounted within the inflation stem housing, the liquid level sensor for sensing a head height within the container, the head height defined as a vertical distance between the upper container surface proximate to the bung opening, and the liquid level beneath the bung opening, the liquid level sensor sends a fill signal to a gas valve, when the head height is greater than a predetermined fill value;
    the gas valve opened when the fill signal is received from the liquid level sensor; and
    the barrel bladder inflated by a pressurized feed of the inflation gas routed through the gas valve, to reduce the head height within the wooden container.

2. The bladder system according to claim 1, further comprising additional sensors associated with the bladder system, the additional sensors inserted into the bung opening of the wooden container.

3. The bladder system according to claim 1, further comprising additional sensors associated with the bladder system, the additional sensors inserted into the wooden container.

4. A bladder system for reducing a head space in a container of a beverage, the bladder system comprising:
    an inflation stem connected to a barrel bladder, the barrel bladder inflatable by filling with an inflation gas;
    the inflation stem anchored within a bung opening of a wooden container, the bung opening located proximate to an upper container surface of the wooden container;
    the inflation stem including an upper stem end and a lower stem end;
    an inflation port proximate to the upper stem end;
    a bladder port proximate to the lower stem end;
    a liquid level sensor for sensing a head height, the head height defined as a vertical distance between the upper container surface and the liquid level beneath the upper container surface, and the liquid level sensor sends a fill signal to a as valve, when the head height is greater than a predetermined fill value;
    the as valve opened when the fill signal is received from the liquid level sensor;
    the barrel bladder inflated by a pressurized feed of the inflation as routed through the as valve, to reduce the head height within the wooden container; and
    the liquid level sensor sends a high alarm signal to a gas valve control to close the gas valve, and the liquid level sensor sends the high alarm signal to a relief port to open the relief port, when the head height is greater than a predetermined low alarm level.

5. The bladder system according to claim 1, wherein:
    the liquid level sensor sends a low alarm signal to a gas valve control to close the gas valve, when the head height is greater than a predetermined low alarm level.

6. The bladder system according to claim 1, wherein:
    the liquid level sensor sends a high alarm signal to a gas valve control to close the gas valve, and the liquid level sensor sends the high alarm signal to a relief port to open the relief port, when the head height is greater than a predetermined low alarm level.

7. The bladder system according to claim 1, wherein:
    the liquid level sensor sends a signal to a gas valve control;
    the inflation stem, and the barrel bladder, the liquid level sensor, the gas valve, and the gas valve control are included in a barrel service mechanism; and
    a control module is connected to and in communication with the barrel service mechanism, and a multiple of a multiple of the control modules, each of the multiple of the control modules are connected to a computer controlled network, with each of the multiple of the control modules connected to an additional barrel service mechanism.

8. The bladder system according to claim 4, wherein:
    the liquid level sensor sends a low alarm signal to a gas valve control to close the gas valve, when the head height is greater than a predetermined low alarm level.

9. The bladder system according to claim 4, wherein:
    the liquid level sensor sends a high alarm signal to a gas valve control to close the gas valve, and the liquid level sensor sends the high alarm signal to a relief port to open the relief port, when the head height is greater than a predetermined low alarm level.

10. The bladder system according to claim 4, wherein:
    the liquid level sensor sends a signal to a gas valve control;
    the inflation stem, and the barrel bladder, the liquid level sensor, the gas valve, and the gas valve control are included in a barrel service mechanism; and
    a control module is connected to and in communication with the barrel service mechanism, and a multiple of a multiple of the control modules, each of the multiple of the control modules are connected to a computer controlled network, with each of the multiple of the control modules connected to an additional barrel service mechanism.

11. The bladder system according to claim 4, further comprising additional sensors associated with the bladder system, the additional sensors inserted into the bung opening of the wooden container.

* * * * *